United States Patent [19]

Lada et al.

[11] 4,104,368

[45] Aug. 1, 1978

[54] COMPOSITION AND METHOD FOR PROTECTING SKIN AND HAIR

[75] Inventors: Arnold Lada, Montclair; James J. Middleton, Orange, both of N.J.

[73] Assignee: Millmaster Onyx Corporation, New York, N.Y.

[21] Appl. No.: 271,206

[22] Filed: Jul. 12, 1972

Related U.S. Application Data

[60] Continuation-in-part of Ser. No. 36,490, May 11, 1970, abandoned, which is a division of Ser. No. 747,500, Jul. 25, 1968.

[51] Int. Cl.$^2$ ............................................. A61K 7/44
[52] U.S. Cl. ........................................ 424/60; 424/315; 424/316; 424/329
[58] Field of Search ................. 424/59, 60, 316, 315, 424/329

[56] References Cited

U.S. PATENT DOCUMENTS

| | | | |
|---|---|---|---|
| 2,634,229 | 4/1953 | de Wet | 424/329 X |
| 3,235,556 | 2/1966 | Wakeman et al. | 260/286 |

FOREIGN PATENT DOCUMENTS

| | | | |
|---|---|---|---|
| 867,135 | 12/1952 | Fed. Rep. of Germany | 424/60 |
| 799,467 | 8/1958 | United Kingdom | 424/60 |

OTHER PUBLICATIONS

McCutcheon, 1968, Detergents & Emulsifiers Annual, p. 208.

*Primary Examiner*—Dale R. Ore
*Attorney, Agent, or Firm*—Arthur A. Jacobs

[57] ABSTRACT

A composition which provides both a conditioning and sun-screening effect for hair and skin wherein the active agent comprises a salt of certain long chain cationic bases and certain acidic substances wherein the acidic moiety provides the sun-screening effect and the cationic moiety provides the tissue conditioning effect. The acidic substances have an acidic or pseudoacidic hydrogen or a lactone thereof, whereas the cationic moiety are long-chain quaternary ammonium salts.

2 Claims, No Drawings

COMPOSITION AND METHOD FOR PROTECTING SKIN AND HAIR

This is a continuation-in-part of co-pending application Ser. No. 36,490, filed May 11, 1970, now abandoned, which is, in turn, a division of application Ser. No. 747,500, filed Jul. 25, 1968.

This invention relates to cosmetic preparations which serve to condition hair and skin, and simultaneously to protect the tissues from the deleterious effect of the ultraviolet region of the spectra of the sun and also of arclamps, sun lamps and the like.

It is well known that certain organic compounds are more or less effective sunscreens, that is, they absorb portions of the ultraviolet range which cause erythema, or reddening, burning and even blistering of human skin. Some of these agents are fluorescent, absorbing the objectionable rays and emitting rays of innocuous wave lengths; others absorb the burn-causing rays and, by so doing, are gradually decomposed. In other cases, the protective mechanism involved is not fully understood.

The radiation range which is most harmful is from about 2894A to about 3120A, the peak being at about 2967A. However, the radiation range down to about 2200A may also cause burning, but is less likely to penetrate the outer or corneous layer of the skin.

The primary object of the present invention is to provide compositions which will simultaneously act as conditioning agents both for the skin and hair, and also screen out a substantial proportion of the erythematous light rays. In this respect, the compositions of the present invention are effective for both sunscreening and conditioning in the range of between about 2200A and about 3120A. These compositions include certain quaternary ammonium salts which are dissolved or suspended in an oily or fatty or creamy medium, or in oil-in-water or water-in-oil emulsion form (as with such agents as glyceryl monostearate and the like).

In general, the compositions embodying the present invention contain salts of certain long-chain cationic bases and certain acidic substances wherein the acidic moiety provides the desirable screening effect, while the cationic moiety provides the tissue conditioning effect. Because these products are cationics, their action is such as to make them substantive to protein (hair and skin). This substantivity provides a long lasting conditioning and sunscreening effect, since the representative compounds are not easily removed by water.

The cationic portion may, if desired, also be chosen to effect some degree of sunscreening. Among others, long-chain isoquinolinium derivatives are in this class.

The cosmetic preparations containing the said conditioning-screening agents may be of the nature of oils, creams, or ointments, or of hair-sprays, or solutions in appropriate solvents (such as alcohol, with or without the addition of polyalkylene oxide derivatives) or in other suitable mediums for the desired type of application.

The ultraviolet absorbing moiety may be any one of a number of substances having an acidic or pseudo-acidic hydrogen, or a lactone thereof, such as p-aminobenzoic acid and its derivatives, salicylic acid and its derivatives malonic acid and its derivatives such as diethyl p-dimethylamino-benzalmalonate and di-isobutyl p-dimethylamino-benzalmalonate, cinnamic acid and its derivatives, such, for example, as the hydroxycinnamic acids and coumarins, umbelliferone, β-methyl umbelliferone, esculetin, tannic and gallic acids, naphthol sulfonic acids, menthyl salicylate, anthranilic acid, and others of like nature.

The cations may be those of such quaternary ammonium salts as alkyl dimethyl benzyl ammonium chloride, alkyl-benzyl trimethyl ammonium chloride, alkyl trimethyl ammonium chloride, alkyl isoquinolinium, alkyl pyridinium, alkyl dimethyl ethyl ammonium bromide. Also alkyl imidazoliniums and amido-imidazoliniums and their urea condensates. In all of the above compounds the alkyl contains from 12 to 24 carbon atoms and, preferably contains 16 to 18 carbon atoms, the latter being most satisfactory as conditioners or creme rinses.

The compounds used in this invention may be prepared by reacting stoichiometrically the alkali metal salts of the sunscreening agents with the halide or other soluble salts of the cationic material; or by reacting the free acids with the hydroxides of the cationics. In this manner, the essentially water-insoluble products may be purified of salt to whatever degree is required, and may be isolated and dehydrated, where such condition is necessary.

On the other hand, the above reactants may be added to a conditioner or creme rinse formulation, and the compounds are then formed in situ.

By the above procedures, such compounds as stearyl dimethyl benzyl para-aminobenzoate, para-aminocinnamate, salicylate, tannate, menthyl salicylate, umbelliferone acetate and the like salts may be prepared. Heptadecyl-N-amino-ethyl imidazoline or the corresponding heptadecyl-N-hydroxyethyl imidazoline may be reacted with the same or other sunscreen acids; or they may be first quaternized, as with benzyl chloride, methyl chloride or bromide, diethylsulfate and the like, and then reacted with salts of the acids.

Any cationic compound of the above classes may be reacted with any of the above acidic screening agents by one skilled in the art, either in situ, or segregated for addition to a formulation.

The following examples are intended merely to illustrate and not to limit the invention.

EXAMPLE 1

10 grams of stearyl dimethyl benzyl ammonium chloride was dispersed in water and isopropanol, and to this, with agitation, was added a stoichiometric amount of sodium salicylate. The mixture was slightly warmed, and the stearyl dimethyl benzyl ammonium salicylate was separated and dried.

An aqueous solution containing 0.05% by weight of this product was found to have an absorptive power for ultraviolet light between 3120A and 2850A, to the same degree as a 0.02% solution of sodium salicylate.

The screening effect is thus approximately that due to the mol fraction of the salicylic content of the compound.

EXAMPLE 2

In the same manner, stearyl dimethyl benzyl ammonium chloride was reacted with sodium para-aminobenzoate. A 0.1% solution of the product and a 0.1% solution of the sodium paraaminobenzoate are equal in absorption in the range between 3080A and 2200A. In this case, the complex is effective to an extent far beyond that of the para-aminobenzoic portion.

EXAMPLE 3

Stearyl dimethyl benzyl ammonium chloride and alkali metal salts of anthranilic acid, umbelliferone, menthyl salicylate, malonic acid, cinnamic acid, tannic acid and naphthol disulfonic acids were reacted to yield the corresponding quaternary ammonium salts of sun-screeing agents, in the manner described above.

EXAMPLE 4

Instead of stearyl dimethyl benzyl ammonium chloride, octadecyl dimethyl menaphthyl ammonium chloride was reacted with the alkali metal salts of the screening agents of Example 3.

EXAMPLE 5

In the same manner as the above, octadecyl isoquinolinium chloride was reacted with the salts of the sun-screening agents of Example 3.

In Examples 4 and 5, the cations contribute to the sun-screening effect because of the photochemical properties of their aromatic double-ring components.

EXAMPLE 6

A creme hair rinse was prepared from the following components:

| Components | Parts by Weight (grams) |
| --- | --- |
| Stearyl dimethyl benzyl ammonium p-aminobenzoate | 3.0 |
| Ethyl alcohol (95%) | 10.0 |
| Cetyl alcohol | 1.0 |
| Water | 86.0 |

This formulation may be prepared by adding to the other components, with agitation, stearyl dimethyl benzyl ammonium chloride and the sodium salt of para-aminobenzoic acid in whatever proportions are required for the particular use.

In the above and in the subsequent examples, coloring agents and perfumes may be added to taste.

EXAMPLE 7

A sun-tan cream was prepared as follows:

| Components | Parts by Weight (grams) |
| --- | --- |
| Stearyl dimethyl benzyl ammonium cinnamate | 5.0 |
| Cetyl alcohol | 4.0 |
| Polyethylene glycol 300 distearate | 1.0 |
| Water | 90.0 |

Instead of the cinnamate, the corresponding salicylate may be used.

EXAMPLE 8

A sun tan oil was prepared by mixing the following:

| Components | Parts by Weight |
| --- | --- |
| Stearyl dimethyl benzyl ammonium para-amino benzoate | 4.0 |
| Heptadecyl-N-amino ethyl imidazolinium anthranilate | 1.0 |
| Sesame oil | 30.0 |
| Peanut oil | 35.0 |
| Mineral oil | 30.0 |

In all of the above examples, the mixtures were prepared at room temperatures and pressures unless otherwise specifically stated. All parts are by weight, unless otherwise specified.

Obviously, many modifications of the present invention are possible in the light of the above teachings. It is, therefore, to be understood that within the scope of the appended claims, the invention may be practiced otherwise than as specifically described.

The invention claimed is:

1. A method of protecting human skin or hair from the effects of erythematous light rays in the range of wave length of between about 2200A and 3120A which comprises applying to said skin or hair an effective amount sufficient to obtain effective radiation absorption within such range of stearyl dimethyl benzyl ammonium p-aminobenzoate.

2. A composition comprising a dispersion of the compound stearyl dimethyl benzyl ammonium p-aminobenzoate in a diluent selected from the group consisting of oil, cream, ointment, spray and a solvent in which said compound is soluble, said compound being present in a sufficient amount to obtain effective radiation absorption in the range of between about 2200A and about 3120A when applied to human skin or hair.

* * * * *